(12) United States Patent
Matsubara et al.

(10) Patent No.: US 10,342,946 B2
(45) Date of Patent: Jul. 9, 2019

(54) CANNULA DEVICE

(71) Applicant: ATOM MEDICAL CORPORATION, Bunkyo-ku, Tokyo (JP)

(72) Inventors: Kazuo Matsubara, Tokyo (JP); Terumi Matsubara, Tokyo (JP); Kenji Kobayashi, Saitama (JP); Shinichi Kobayashi, Saitama (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 565 days.

(21) Appl. No.: 14/728,096

(22) Filed: Jun. 2, 2015

(65) Prior Publication Data
US 2016/0067440 A1 Mar. 10, 2016

(30) Foreign Application Priority Data
Sep. 5, 2014 (JP) .................................. 2014-181179

(51) Int. Cl.
*A61M 16/08* (2006.01)
*A61M 16/06* (2006.01)

(52) U.S. Cl.
CPC .... *A61M 16/0672* (2014.02); *A61M 16/0666* (2013.01); *A61M 16/0816* (2013.01); *A61M 2202/0208* (2013.01)

(58) Field of Classification Search
CPC .......... A61M 16/0666; A61M 16/0672; A61M 2202/0208; A61M 16/0816;
(Continued)

(56) References Cited

U.S. PATENT DOCUMENTS 4,723,948 A * 2/1988 Clark .................... A61M 39/12
285/243
4,919,462 A 4/1990 Matsui et al.
(Continued)

FOREIGN PATENT DOCUMENTS

CN 1905917 A 1/2007
JP S64-26318 A 1/1989
(Continued)

OTHER PUBLICATIONS

Office Action, and English language translation thereof, in corresponding Japanese Application No. 2015-075298, dated Apr. 25, 2017, 8 pages.

*Primary Examiner* — Colin W Stuart
*Assistant Examiner* — Douglas Y Sul
(74) *Attorney, Agent, or Firm* — Brinks Gilson & Lione

(57) ABSTRACT

A cannula device including: a nasal cannula having nasal pipes; respiration-gas flow tubes connected to the nasal cannula; an adaptor pipe communicated with the respiration-gas flow tubes; a connector pipe removably attached to the adaptor pipe; and a respiration-gas supplying tube connected to the connector pipe, in the cannula device, one of the adaptor pipe and the connector pipe is a female member having a receiving part and the other is a male member having an inserting part; and the male member is removably inserted into the female part, and the cannula device further including: a ring-shape part formed on a base-end part of the inserting part as a protruding ridge or a recessed groove extending on whole circumference of the inserting part; and a lock piece formed on the receiving part, having a projection part locking the ring-shape part of the inserting part inserted in the receiving part.

2 Claims, 5 Drawing Sheets

(58) Field of Classification Search
CPC ...... A61M 39/1011; A61M 2039/1027; A61M 2039/1077
USPC .......................................................... 285/406
See application file for complete search history.

(56) References Cited

U.S. PATENT DOCUMENTS

| | | | | |
|---|---|---|---|---|
| 6,099,519 | A * | 8/2000 | Olsen | A61M 16/0463 604/171 |
| 6,568,716 | B1 | 5/2003 | Fieber | |
| 6,997,177 | B2 * | 2/2006 | Wood | A61M 16/0666 128/200.24 |
| 7,350,834 | B2 * | 4/2008 | Ryhman | F16L 23/04 285/406 |
| 8,136,527 | B2 * | 3/2012 | Wondka | A61M 16/00 128/200.24 |
| 2004/0226566 | A1 | 11/2004 | Gunaratnam et al. | |
| 2008/0041391 | A1 * | 2/2008 | Worley | A61M 16/0465 128/207.14 |
| 2010/0025987 | A1 * | 2/2010 | Nagaya | F16L 37/144 285/275 |
| 2013/0249211 | A1 | 9/2013 | Yang | |
| 2015/0032089 | A1 * | 1/2015 | Way | A61M 39/1011 604/535 |

FOREIGN PATENT DOCUMENTS

| | | |
|---|---|---|
| JP | 2003-507687 A | 2/2003 |
| JP | 2006-518231 A | 8/2006 |
| JP | 2008-163976 A1 | 7/2008 |
| JP | 2011-15731 A | 1/2011 |

* cited by examiner

CANNULA DEVICE

BACKGROUND OF THE INVENTION

Field of the Invention

The present invention relates to a cannula device for supplying respiration gas such as oxygen gas to a human body.

Priority is claimed on Japanese Patent Application No. 2014-181179 filed Sep. 5, 2014, the content of which is incorporated herein by reference.

Description of the Related Art

Conventionally, artificial respirators sending respiration gas including specified quantity of oxygen to a respiratory tract of a patient, devices for oxygen inhalation therapy, and the like are known. The respiration gas sent from these devices is supplied to a human body through a cannula device. The cannula device has a structure in which a plurality of tubes are connected to a nasal cannula installed on nares of a human body, the tubes are connected to a respiration gas-supplying device such as an artificial respirator, an oxygen generator or the like.

For example, a conventional cannula device is disclosed in Japanese Unexamined Patent Application, First Publication No. 2011-015731 (hereinafter, "JP '731"). The cannula device of JP '731 is provided with: a flexible nasal cannula with a hollow structure; a pair of left and right flexible and relatively short first oxygen-supplying tubes as respiration gas-supplying tubes in which end parts thereof are connected to both ends of the nasal cannula respectively; a flexible Y-shape connector connecting the other ends of the first oxygen-supplying tubes to an end of a flexible and relatively short second oxygen-supplying tube as a respiration gas-supplying tube; and a connector fixed to the other end of the second oxygen-supplying tube. Further, the connecter is detachably attached to a connector at an end of a third tube for supplying oxygen gas. The third tube is relatively long and flexible tube for supplying the respiration gas, and is connected to the respiration gas-supplying device.

SUMMARY OF THE INVENTION

Problems to be Solved by the Invention

In the cannula device, the connector at the nasal cannula and the connector of the supplying tube at the respiration gas-supplying device are detachable to each other; therefore, it is necessary to give care not to be detached carelessly by a connection mistake and the like. In a case in which the respiration gas is forcibly supplied to a human body when a patient goes into cardiopulmonary arrest, or in a high-flow therapy supplying the respiration gas to the patient with a higher flow than expiration of the patient, which is remarkable in recent years, the respiration gas is supplied to the human body with a higher flow quantity than a conventional flow quantity. Particularly, when the respiration gas is supplied with the high flow quantity, it is necessary to prevent from being detached. On the other hand, it is desirable to be attachable and detachable easily in an emergency.

The present invention is achieved in consideration of the above circumferences, and has an object to provide a cannula device in which a tube of a nasal cannula and a supplying tube of a respiration gas-supplying device are reliably attachable and detachable with ease.

Means for Solving the Problem

A cannula device according to the present invention includes: a nasal cannula including a pair of nasal pipes mounted on nares of a human body; a pair of respiration-gas flow tubes which are connected to the nasal cannula and communicated with the nasal pipes; an adaptor pipe which is communicated with the respiration-gas flow tubes and connected to ends of the respiration-gas flow tubes; a connector pipe which is removably attached to the adaptor pipe; and a respiration-gas supplying tube which is connected to the connector pipe, the cannula device in which: one of the adaptor pipe and the connector pipe is a female member having a receiving part and the other is a male member having an inserting part, and the male member is removably inserted into the female part, and the cannula device further including: a ring-shape part which is formed on an outer surface of a base-end part of the inserting part having a shape of a protruding ridge or a recessed groove extending on whole circumference of the inserting part; and a lock piece which is formed on the receiving part and has a projection part which locks the ring-shape part of the inserting part which is inserted into the receiving part.

By locking the ring-shape part and the lock piece together in a state in which the male member is inserted in the female member as one of the connector pipe and the adaptor pipe is the female member (i.e., the receiving part) and the other of them is the male member (i.e., the inserting part), it is possible to maintain a connection state of the connector pipe and the adaptor pipe to each other. In this case, since the ring-shape part to be locked by the lock piece is formed along a peripheral direction, it is possible reliably to lock the connector pipe and the adaptor pipe regardless of relative positions of the connector pipe and the adaptor pipe along the peripheral direction. Accordingly, it is possible to connect the connector pipe and the adaptor pipe with ease only by inserting regardless of the relative positions along the peripheral direction.

In addition, either of the connector pipe and the adaptor pipe may be the inserting part (i.e., the male member), and the other is the receiving part (i.e., the female member). It is enough that the lock piece is provided on an outer surface of the female member (i.e., the receiving part).

In the cannula device according to the present invention, in a case in which the ring-shape part is the protruding ridge, it is preferable that the lock piece be rotatably held by a hinge shaft fixed on an outer surface of the receiving part, and be formed to have an arc-shape along a part of the outer surface of the receiving part; and the projection part be formed to protrude radially inward, and arranged at a position nearer to the base-end part of the inserting part than the ring-shape part formed as the protruding ridge in a state in which the inserting part is inserted in the receiving part.

Alternatively, in the cannula device according to the present invention, in a case in which the ring-shape part is the recessed groove, it is preferable that the lock piece be rotatably held by a hinge shaft fixed on an outer surface of the receiving part, and be formed to have an arc-shape along a part of the outer surface of the receiving part; and the projection part be formed to protrude radially inward, and fitted into the ring-shape part formed as the recessed groove in a state in which the inserting part is inserted in the receiving part.

In this case, it is possible to lock or release the connection of the connector pipe and the adaptor pipe by closing or opening the arc-shaped lock piece around the hinge shaft with excellent usability.

In the cannula device according to the present invention, it is desirable that a fastening part be provided on an outer surface of the receiving part so as to fasten the lock piece in a state of locking the ring-shape part.

By providing the fastening part so as to fasten the lock piece, it is possible to maintain the connection of the adaptor pipe and the connector pipe. Accordingly, even when the respiration gas is supplied to the human body with higher flow quantity than in an ordinary case, it can be reliably prevented from falling out.

Effects of the Invention

According to the cannula device of the present invention, when attaching or detaching the adaptor pipe and the connector pipe, it is not necessary to careful in the relative positions along the peripheral direction, so that it is easy to attach or detach the pipes. Moreover, since the adaptor pipe and the connector pipe are locked by the lock piece, it is possible to reliably maintain the connection state of the nasal cannula and the respiration-gas supplying tube.

DETAILED DESCRIPTION OF THE INVENTION

Below, an embodiment of a cannula device according to the present invention will be described referring drawings.

Figure 1:
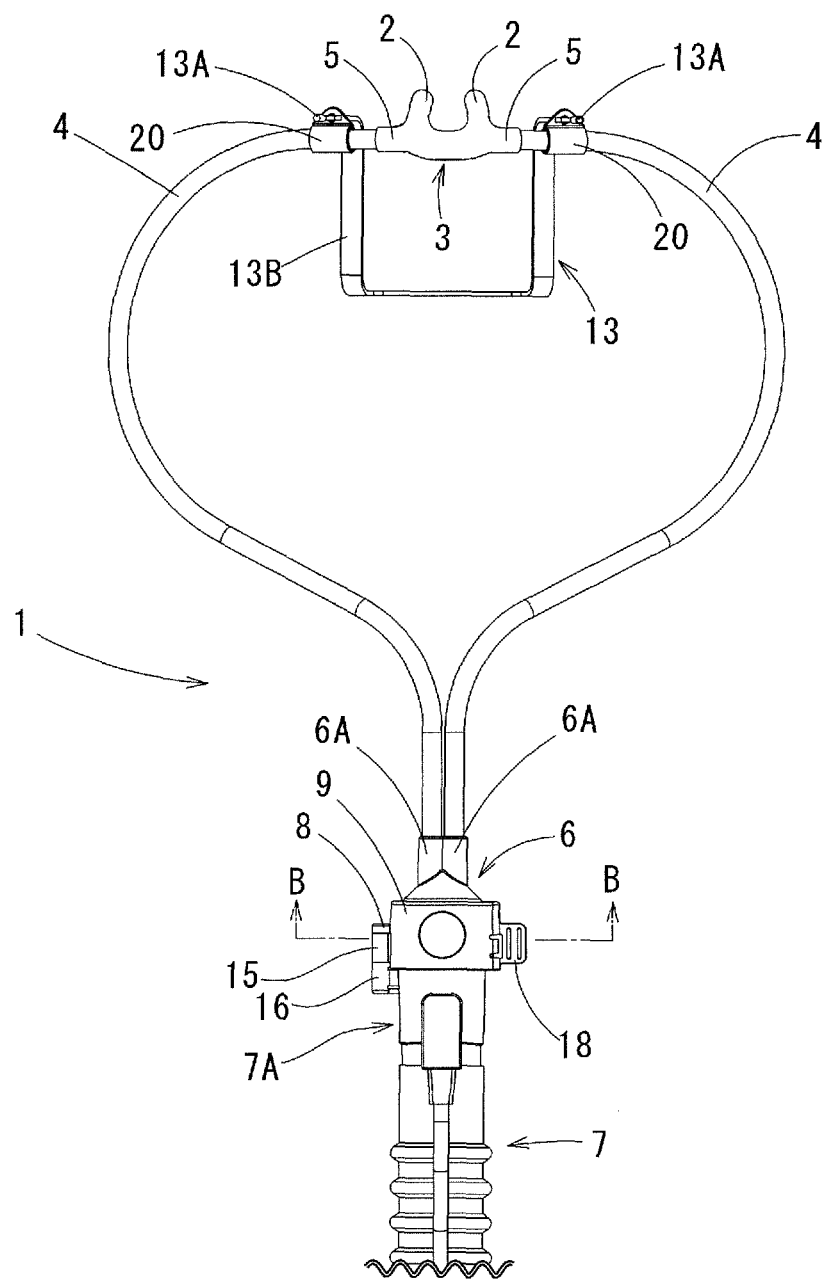
FIG. 1 is a front view showing an embodiment of a cannula device according to the present invention.
Figure 2:
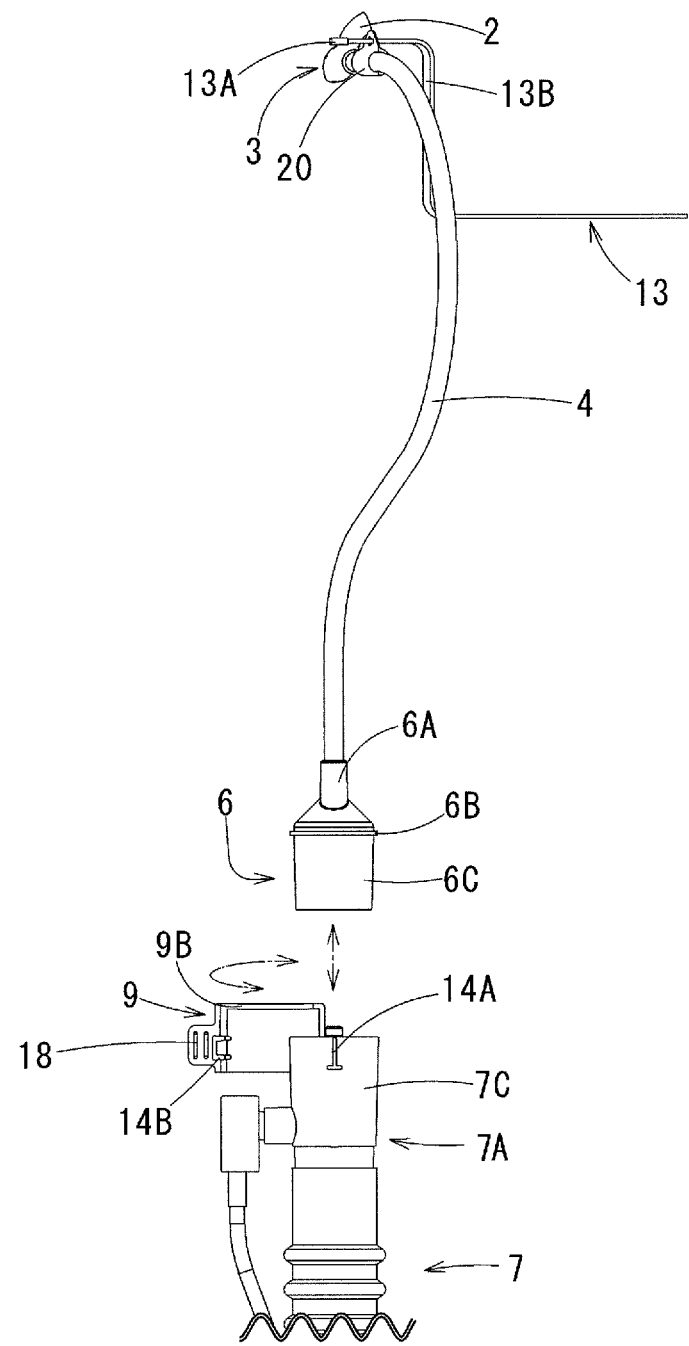
FIG. 2 is a left side view showing an adaptor pipe and a connector pipe in an unconnected state in the cannula device of FIG. 1.

As shown in FIG. 1 and FIG. 2, a cannula device 1 is provided with: a nasal cannula 3 having a pair of nasal pipes 2 mounted on nares of a patient; a pair of respiration-gas flow tubes 4 which are connected to the nasal cannula 3 and communicated with the nasal pipes 2; an adaptor pipe 6 (i.e., a male member) which is communicated with the respiration-gas flow tubes 4 and connected to ends of the respiration-gas flow tubes 4; a connector pipe 7A (i.e., a female member) which is removably attached to the adaptor pipe 6; a respiration-gas supplying tube 7 which is connected to the connector pipe 7A; a lock door (i.e., a lock piece) 9 which is rotatably held on an outer surface of the connector pipe 7A; and a fixing member 13 fixing the nasal cannula 3 on a head of the patient.

The nasal cannula 3 includes the nasal pipes 2 extending upward in FIG. 1 and connection-end parts 5 which are communicated with the nasal pipes 2 and open at left and right sides with interposing the nasal pipes 2. The nasal cannula 3 is formed to follow a surface of a face when being mounted on the patient by curving a center of the left and right (i.e., a vicinity of the nasal pipes 2). The nasal cannula 3 as a whole is made of soft synthetic resin such as styrene elastomer, silicone rubber, urethane, or the like.

One ends of the respiration-gas flow tubes 4 are connected respectively to the connection-end parts 5 of the nasal cannula 3; and the other ends thereof are connected to the adaptor pipe 6. As the respiration-gas flow tubes 4, either of a normal tube for general-purpose and a non-crush tube in which ribs are formed on an inner surface thereof along a longitudinal direction so as not to be clogged even if it is folded can be used.

The fixing member 13 is attached to a pair of brackets 20 mounted respectively on the two respiration-gas flow tubes 4. The fixing member 13 is an elastic cord in the present embodiment. The elastic cord has top-end parts 13A which are hardened as thin rods and a body part 13B of a stretchable band-shape.

In the present embodiment, the connector pipe 7A which is the female member having a receiving part 7C and the adaptor pipe 6 which is the male member having an inserting part 6C are provided so as to be inserted to or detached from each other.

Figure 3:
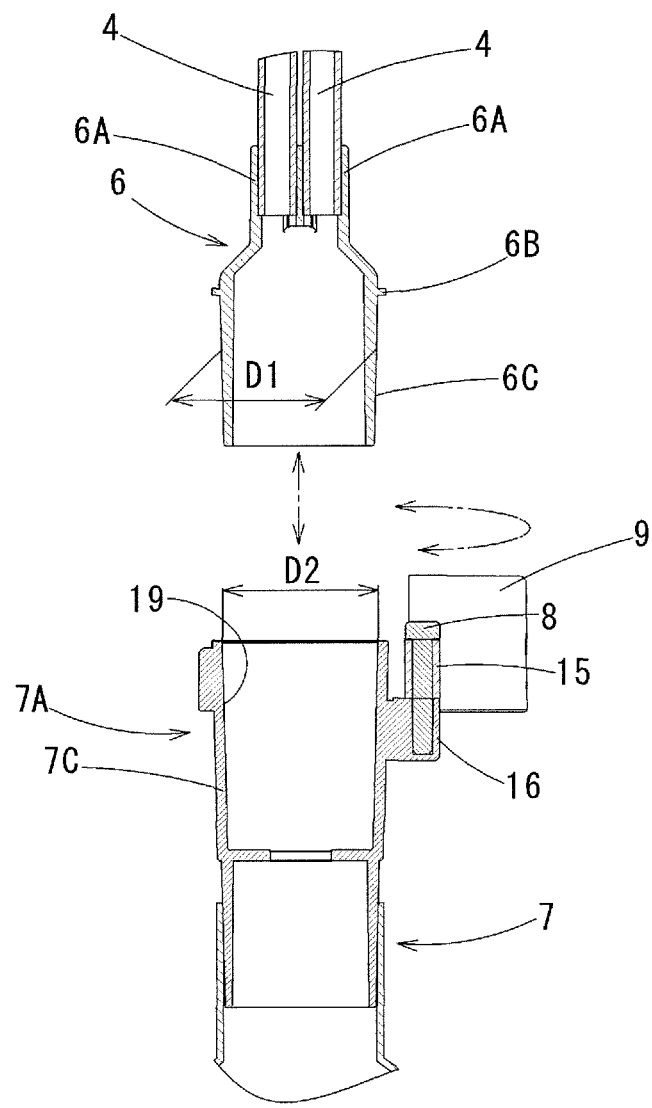
FIG. 3 is a vertical sectional view showing the adaptor pipe and the connector pipe in the unconnected state in the cannula device of FIG. 1.

As shown in FIG. 3, the adaptor pipe 6 is formed into one piece by hard synthetic resin including a pair of introducing pipes 6A to which the two respiration-gas flow tubes 4 are connected respectively and the inserting part 6C having substantially a cylindrical shape communicating with the introducing pipes 6A. The adaptor pipe 6 connects one flow of the respiration-gas supplying tube 7 to two flows of the respiration-gas flow tubes 4.

An outer surface of the inserting part 6C of the adaptor pipe 6 is formed to have a tapered shape in which a diameter thereof is gradually reduced toward a top-end part so that an outer diameter D1 at a middle position along a longitudinal direction is a same as an inner diameter D2 of a tip opening of the receiving part 7C. A flange-like ring-shape part 6B is formed into a protrude ridge extending along whole circumference on a base-end part of the inserting part 6C.

The connector pipe 7A removably connected to the adaptor pipe 6 is connected to an end of the respiration-gas supplying tube 7 having a bendable and extendable bellows-shape. The connector pipe 7A is made from hard synthetic resin; and as shown in FIG. 2 and FIG. 3, the connector pipe 7A includes: the cylindrical receiving part 7C which receives the inserting part 6C of the adaptor pipe 6; a supporting part 16 which rotatably supports the lock door 9 on an outer surface of the receiving part 7C; and a fastening part 14A which fastens an end of the lock door 9 when the lock door 9 covers a part of the ring-shape part 6B of the adaptor pipe 6 (refer to FIG. 5).

The receiving part 7C has a tapered inner surface 19 in which the inserting part 6C of the adaptor pipe 6 can be inserted regardless of relative rotational positions to each other. Since the inner diameter D2 of the tip opening of the receiving part 7C and the outer diameter D1 at the middle position along the longitudinal direction of the tapered inserting part 6C are the same dimension, the adaptor pipe 6 and the connector pipe 7A are air-tightly connected reliably, so that leakage of the respiration gas or the like can be prevented.

A hinge shaft 8 which is parallel to an axis direction is fixed to the supporting part 16. For example, in the present embodiment, the hinge shaft 8 is fixed at a lower end part in a state in which an upper end of the hinge shaft 8 is protruded.

Figure 4:
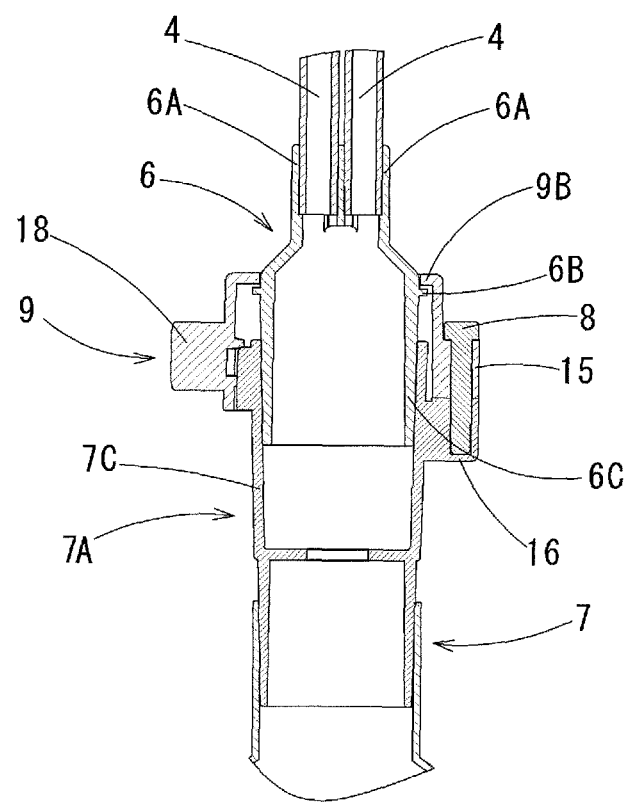
FIG. 4 is a vertical sectional view showing the adaptor pipe and the connector pipe in a connected state in the cannula device of FIG. 1.
Figure 5:
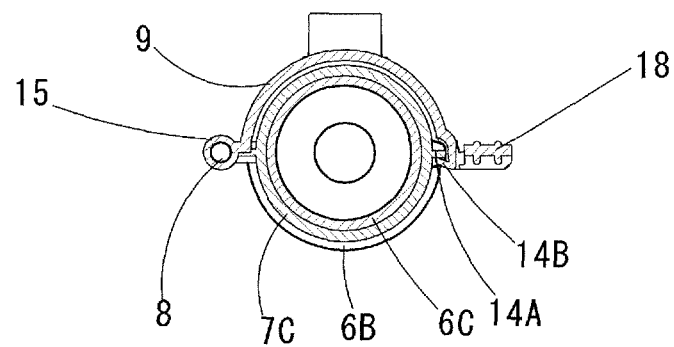
FIG. 5 is a sectional view taken along the line B-B in FIG. 1.
Figure 6:
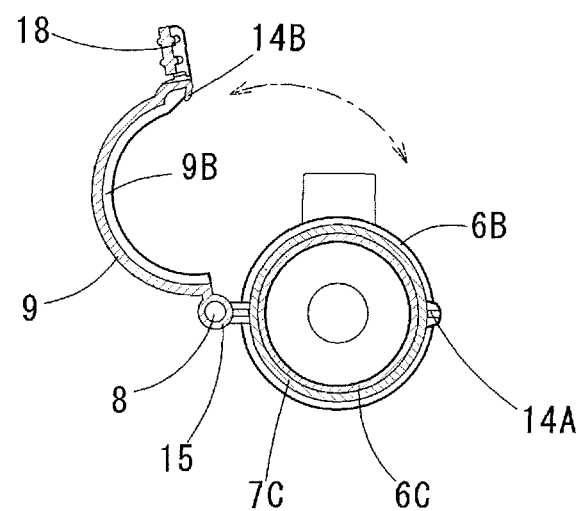
FIG. 6 is a sectional view showing a state in which a lock piece of FIG. 5 is open.

As shown in FIG. 4 to FIG. 6, the lock door 9 is formed as an arc-plate shape having a slightly larger inner diameter than an outer diameter of the receiving part 7C; and has: a through hole 15 formed at an end part along a circumference direction and penetrated by the hinge shaft 8; a fastening hook 14B protruding inward from the other end part along the circumference direction; a lever part 18 formed outside the fastening hook 14B; and a projection part 9B protruding radially inward from an upper end part along the circumference direction.

As shown in FIG. 4, the projection part 9B has an L-hook-like shape in a vertical section of the lock door 9 and is set so as to arranged at a position nearer to the base-end part of the adaptor pipe 6 than the ring-shape part 6B of the inserting part 6C when the inserting part 6C of the adaptor pipe 6 is inserted in the receiving part 7C of the connector pipe 7A, that is to say, so that the ring-shape part 6B is arranged between the projection part 9B and the tip opening of the receiving part 7C.

Next, a procedure for connecting the adaptor pipe 6 and the connector pipe 7A will be described. FIG. 3 shows a vertical sectional view of a state in which the adaptor pipe 6 and the connector pipe 7A are unconnected and the lock door 9 is open. FIG. 5 shows a sectional view taken along the line B-B of FIG. 1 in which the lock door 9 is closed. FIG. 6 shows a sectional view of a state in which the lock door 9 is open.

First, the inserting part 6C of the adaptor pipe 6 is inserted into the receiving part 7C of the connector pipe 7A in a state in which the lock door 9 is open (FIG. 6). At this time, the inserting part 6C is inserted so that the position having the outer diameter D1 is entirely entered in the receiving part 7C. Next, by rotating the lock door 9 so that the projection part 9B is at the position nearer to the base-end part than the ring-shape part 6B and an arc-shape plate part covers the part of the outer surface of the inserting part 6C. Then, by hooking the fastening hook 14B of the lock door 9 to the fastening part 14A provided on the outer peripheral surface of the receiving part 7C, the lock door 9 is fastened so as not to be rotated (FIG. 5). By fastening the lock door 9, the projection part 9B of the lock door 9 is arranged so as to be over an upper surface of the ring-shape part 6B of the adaptor pipe 6, so that adaptor pipe 6 can be prevented from being detached.

The projection part 9B of the lock door 9 is protruded radially inward; and the ring-shape part 6B of the adaptor pipe 6 is formed extending along whole circumference. Accordingly, the connector pipe 7A and the adaptor pipe 6 can be connected regardless of the relative rotational positions, and the lock state can be reliably maintained. Therefore, it is not necessary to mind the relative rotational position, but the adaptor pipe 6 can be inserted into the connector pipe 7A, and the pipes are very easy to be attached to or detached from each other.

Moreover, since the lock door 9 is fixed to the receiving part 7C by the fastening part 14A and the fastening hook 14B, the connection state of the adaptor pipe 6 and the connector pipe 7A can be maintained. Accordingly, even when the respiration gas is supplied to a human body with higher flow quantity than in an ordinary case and inner pressure of the pipe is high; it can be reliably prevented from falling out.

The present invention is not limited to the above-described embodiments and various modifications may be made without departing from the scope of the present invention.

Though the adaptor pipe 6 is inserted into the connector pipe 7A in the above embodiment, an adaptor pipe of the nasal cannula side may be a female member and a connector pipe of the respiration-gas supplying tube side may be a male member, so that the connector pipe may be inserted into the adaptor pipe.

Though the ring-shape part 6B of the adaptor pipe 6 is formed into a ring shape protruding from the outer surface of the inserting part 6C in the above embodiment, it may be a recessed groove shape formed by recessing the outer surface of the inserting part.

Though the lock door (i.e., the lock piece) 9 is formed as the arc-plate shape in the above embodiment, a lock piece may be formed as an arc-rod. Furthermore, it is necessary that the lock piece has a shape which can fasten the ring-shape part, but it is not necessary to have an arc shape.

Though the fastening part 14A hooking the fastening hook 14B of the lock door (i.e., the lock piece) 9 is provided in the above embodiment, the fastening structure of the lock piece is not limited to the embodiment. For example, a lock piece may be formed to have a length along the circumferential direction slightly larger than a half of the outer surface of the receiving part and to be elastically deformable so as to hook the outer surface of the receiving part by the elasticity thereof.

What is claimed is:

1. A cannula device comprising:
a nasal cannula including a pair of nasal pipes;
a pair of respiration-gas flow tubes connected to the nasal cannula so that the pair of respiration-gas tubes are communicated with the pair of nasal pipes;
a respiration-gas supplying tube configured to supply respiration gas to the pair of respiration-gas flow tubes;
first and second connector pipes configured for the second connector pipe to be insertable into the first connector pipe so that the first and second connector pipes are connectable to each other in a length direction to establish communication between the respiration-gas supplying tube and the pair of respiration-gas flow tubes, one connector pipe selected from the first and second connector pipes comprising a stopper formed in a circumference of said one connector pipe, and the other connector pipe of the first and second connector pipes having first and second circumferential locations defined at a circumferential interval in a circumference of the other connector pipe, the other connector pipe further comprising a hinge at the first circumferential location and a catcher at the second circumferential location, wherein the first connector pipe has a receiver end having a diameter (D), and the second connector pipe has an inserting end having a diameter (d) smaller than the diameter (D) and an outer surface extensive in an axis direction of the second connector pipe from the inserting end toward an end of the second connector pipe opposite to the inserting end, the connection surface being tapered with a diameter progressively increasing from the diameter (d) to greater than the diameter (D) as a point at which the diameter is measured goes away from the inserting end along the outer surface so that the inserting end of the second connector pipe is insertable into the receiver end of the first connector pipe, and the receiver end of the first connector pipe is held in tight contact with the outer surface of the second connector pipe; and
an arcuate lock piece having a first end and a second end and being provided separately from the other connector pipe, the first end being attached to the hinge at the first circumferential location of the other connector pipe for rotation of the lock piece around the hinge in a plane perpendicular to an axis of the other connector pipe, the second end being extensive from the first end sufficiently to reach at the second circumferential location of the other connector pipe when the lock piece is rotated around the hinge onto the circumference of the other connector pipe, the second end being formed with a hook configured to engage with the catcher at the second circumferential location of the other connector pipe, wherein the hook engages with the catcher solely by rotation of the lock piece around the hinge in the plane perpendicular to the axis of the other connector pipe and holds the lock piece on the circumference of the other connector pipe solely by engagement of the hook with the catcher, the lock piece comprising a latch separate from the hook and configured to engage with the stopper on said one connector pipe so that when the hook of the lock piece is engaged with the catcher, the latch engages with the stopper to keep the first and second connector pipes from being separate in the length direction from each other, and the lock piece further comprising a lever part extending outwardly from the second end of the lock piece, wherein the lever part is operable to engage or disengage the hook with or from the catcher.

2. The cannula device according to claim 1, wherein:

one of the latch and the stopper comprises a protruding ridge, and the other thereof comprises a groove configured to engage with the protruding ridge.

* * * * *